United States Patent [19]

Pfiffner

[11] 4,384,116
[45] May 17, 1983

[54] PROCESS FOR THE PREPARATION OF MORPHOLINE AND PIPERIDINE DERIVATIVES

[75] Inventor: Albert Pfiffner, Bülach, Switzerland

[73] Assignee: Hoffmann-La Roche Inc., Nutley, N.J.

[21] Appl. No.: 230,196

[22] Filed: Feb. 2, 1981

Related U.S. Application Data

[63] Continuation of Ser. No. 61,952, Jul. 30, 1979, abandoned.

[30] Foreign Application Priority Data

Aug. 8, 1978 [CH] Switzerland ............... 8407/78

[51] Int. Cl.³ ............... C07D 265/30; C07D 295/02; C07D 295/06
[52] U.S. Cl. ............... 544/178; 544/106; 546/192
[58] Field of Search ............... 544/106, 178; 546/192

[56] References Cited

U.S. PATENT DOCUMENTS 3,965,105  6/1976  Zenitz ............... 546/192

OTHER PUBLICATIONS

European Patent Specification No. 333, (6-16-78).
Krauch et al., *Reactionen der Organischen Chemie*, (1976), pp. 103-105.
Mathieu et al., *Formation of C-C Bonds*, vol. II (1975), pp. 312 and 335.
Olah, *Friedel-Crafts and Related Reactions*, vol. II, pt. 1 (1964), pp. 576-577.
Olah, *Friedel-Crafts and related Reactions*, vol. III, pt. 2 (1964), pp. 1230—1231.
Volkou et al., *Do Klady Akademii Nauk*, SSSR, 133 (1960), pp. 869-872.
Morrison et al., *Organic Chemistry*, 2nd Ed. (1970), pp. 375-377.

*Primary Examiner*—Robert W. Ramsuer
*Attorney, Agent, or Firm*—Jon S. Saxe; George M. Gould; John J. Maitner

[57] ABSTRACT

The invention relates to an improved process for the preparation of fungicidally active compounds of the formula

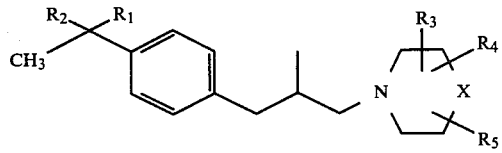

wherein $R_1$ and $R_2$ individually are lower alkyl of from 1 to 4 carbons or halo-(lower alkyl) of from 1 to 4 carbons or $R_1$ and $R_2$ together with the carbon to which they are attached form a 3 to 7 membered cycloalkyl ring or lower alkyl-substituted cycloalkyl of from 4 to 9 carbons, $R_3$, $R_4$ and $R_5$ individually are hydrogen or lower alkyl of from 1 to 4 carbons and X is methylene or oxygen, and salts of those compounds which are basic.

The improved process comprises the reaction of a compound of the formula,

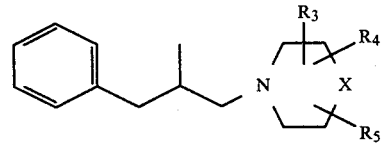

wherein $R_3$, $R_4$, $R_5$ and X have the significance given hereinabove, with a compound which forms a carbonium ion of the formula

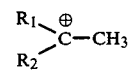

wherein $R_1$ and $R_2$ have the significance as given hereinabove.

6 Claims, No Drawings

PROCESS FOR THE PREPARATION OF MORPHOLINE AND PIPERIDINE DERIVATIVES

This is a continuation of application Ser. No. 61,952 filed July 30, 1979 now abandoned.

BACKGROUND OF THE INVENTION

Fungicidal compounds, as well as compositions and methods for their use, are described in co-pending U.S. patent application Ser. Nos. 853,007 abandoned and 853,018 now U.S. Pat. No. 4,241,058, both filed Nov. 18, 1977. These compounds have the formula

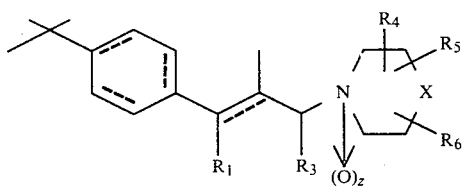

wherein $R_1$ and $R_3$ individually are hydrogen or methyl; $R_4$, $R_5$ and $R_6$ are hydrogen, alkyl of 1 to 4 carbons or any two of $R_4$, $R_5$ and $R_6$ can each be bound to the same carbon to form a fused alicyclic or aromatic 6-membered ring; X is methylene or oxygen; Z is 0 or 1 and ... signifies that the bond can be hydrogenated.

Processes for the preparation of these compounds are described in the aforesaid U.S. patent application Ser. Nos. 853,007 abandoned and 853,018 now U.S. Pat. No. 4,241,058. Processes for the preparation of related compounds are also described in German Offenlegungsschriften Nos. 2,656,747, 2,752,096 and 2,752,135.

SUMMARY OF THE INVENTION

An improved process for the preparation of morpholine and piperidine derivatives of the formula

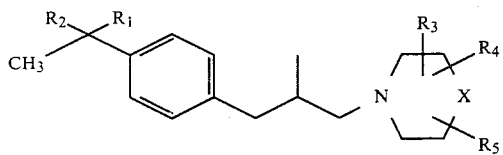

wherein $R_1$, $R_2$, $R_3$, $R_4$, $R_5$ and X are as described hereinbelow, is disclosed.

DETAILED DESCRIPTION OF THE INVENTION

This invention is directed to an improved process for the preparation of fungicidally active morpholine and piperidine derivatives of the formula,

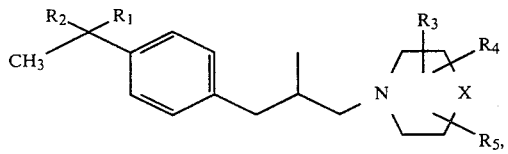

wherein $R_1$ and $R_2$ individually are lower alkyl of from 1 to 4 carbons or halo-(lower alkyl) of from 1 to 4 carbons or $R_1$ and $R_2$ together with the carbon to which they are attached form a 3- to 7-membered cycloalkyl ring or lower alkyl-substituted cycloalkyl of from 4 to 9 carbons, $R_3$, $R_4$ and $R_5$ individually are hydrogen or lower alkyl of from 1 to 4 carbons and X is methylene or oxygen, and salts of those compounds which are basic.

The term "lower alkyl" of from 1 to 4 carbons means either straight-chain or branched-chain hydrocarbon groups such as, e.g. methyl, ethyl, propyl, isopropyl, butyl, isobutyl and tert.butyl.

The term "halo-(lower alkyl)" means a lower alkyl group in which one of the hydrogens has been replaced by halogen, preferably fluorine, chlorine or bromine.

The term "cycloalkyl" means an alicyclic hydrocarbon group of from 3 to 7 carbons such as, e.g. cyclopropyl, cyclobutyl, cyclopentyl, cyclohexyl and cycloheptyl.

The salts of the compounds of formula I which are basic include salts with physiologically acceptable acids. The preferred salts include those formed with hydrohalic acids (e.g. hydrochloric acid and hydrobromic acid), phosphoric acid, nitric acid, monofunctional and bifunctional carboxylic acids and hydroxycarboxylic acids (e.g. acetic acid, maleic acid, succinic acid, fumaric acid, tartaric acid, citric acid, salicyclic acid, sorbic acid and lactic acid) and sulfonic acids (e.g. 1,5-naphthalene-disulfonic acid). These salts are prepared by known procedures.

Preferred compounds of formula I include:
1-[3-(p-tert.butyl-phenyl)-2-methyl-propyl]-piperidine,
1-[3-(p-tert.butyl-phenyl)-2-methyl-propyl]-3-methyl-piperidine,
1-[3-(p-tert.butyl-phenyl)-2-methyl-propyl]-3,5-dimethyl-piperidine,
4-[3-(p-tert.butyl-phenyl)-2-methyl-propyl]-2,6-dimethyl-morpholine,
1-[3-[p-(2-chloro-1,1-dimethyl-ethyl)-phenyl]-2-methyl-propyl]-piperidine,
1-[3-[p-(2-chloro-1,1-dimethyl-ethyl)-phenyl]-2-methyl-propyl]-3,5-dimethyl-piperidine,
4-[3-[p-(2-chloro-1,1-dimethyl-ethyl)-phenyl]-2-methyl-propyl]-2,6-dimethyl-morpholine,
1-[3-(p-tert.amyl-phenyl)-2-methyl-propyl]-piperidine,
1-[3-(p-tert.amyl-phenyl)-2-methyl-propyl]-3-methyl-piperidine,
1-[3-(p-tert.amyl-phenyl)-2-methyl-propyl]-3,5-dimethyl-piperidine,
4-[3-(p-tert.amyl-phenyl)-2-methyl-propyl]-2,6-dimethyl-morpholine,
1-[3-[p-(1-cyclohexyl-1-methyl)-phenyl]-2-methyl-propyl]-piperidine,
1-[3-[p-(1-cyclohexyl-1-methyl)-phenyl]-2-methyl-propyl]-3,5-dimethyl-piperidine
and
4-[3-[p-(1-cyclohexyl-1-methyl)-phenyl]-2-methyl-propyl]-2,6-dimethyl-morpholine.

The compounds of formula I are fungicidally active. They are especially suitable for the control of fungi in both agriculture and in horticulture.

The morpholine and piperdine derivatives of formula I are prepared, in the improved process of this invention, by reacting a compound of the formula,

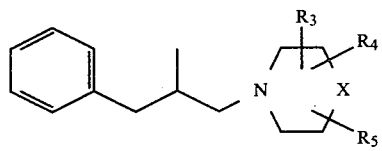

wherein R₃, R₄, R₅ and X have the significance as given hereinabove, with a compound which forms a carbonium ion of the formula

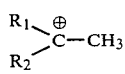   III wherein R₁ and R₂ have the significance as given hereinabove.

Using the improved process of this invention, compounds of formula I are prepared, in comparison to the processes described, for example, in German Offenlegungsschriften Nos. 2,656,747; 2,752,096 and 2,752,135, in improved yields, with less operative steps and with cheaper starting materials.

Compounds of formula II and salts of those compounds of formula II which are basic are prepared by mixing the compound of the formula

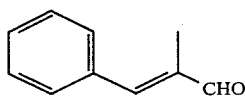   IV with a compound of the formula,

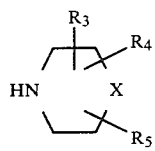   V wherein R₃, R₄ and R₅ are hydrogen atom or lower alkyl of from 1 to 4 carbons and X is methylene or oxygen.

The mixture is catalytically hydrogenated. If desired, a basic compound thus obtained can be converted to a salt.

The usual hydrogenation catalysts such as platinum, Raney-nickel or palladium can be used for the catalytic hydrogenation, a 5% palladium/carbon catalyst is especially preferred.

An organic solvent (e.g. an alcohol such as methanol) is preferably used as the solvent for the catalytic hydrogenation. The temperature is not critical, but generally ranges from about 0° C. to about 50° C.

When at least two of R₃, R₄ and R₅ are lower alkyl and are not attached to the same carbon, compounds of formula V can be used in the form of the pure isomer if desired.

Some of the compounds of formula II are novel and are part of this invention.

Preferred compounds of formula II are:
1-(2-Methyl-3-phenyl-propyl)-piperidine,
1-(2-methyl-3-phenyl-propyl)-3-methyl-piperidine,
1-(2-methyl-3-phenyl-propyl)-3,5-dimethyl-piperidine and
4-(2-methyl-3-phenyl-propyl)-2,6-dimethyl-morpholine.

Preferred compounds which form a carbonium ion of formula III are alkenes such as isobutylene, 3-chloro-2-methyl-1-propene and 1-methylcyclohexene, alcohols, especially tert.alcohols such as tert.butanol and 2-methyl-2-butanol, and secondary alcohols such as 2-methylcyclohexanol and 4-methylcyclohexanol.

The alkylation of a compound of formula II is carried out using an amount of a Friedel-Crafts catalyst sufficient for the reaction. Suitable catalysts are such known Friedel-Crafts catalysts as aluminium chloride, iron chloride, zinc chloride, boron trifluoride, tin chloride, hydrogen fluoride, sulfuric acid and phosphoric acid. Sulfuric acid is especially preferred for the process of the instant invention.

The use of an inert organic solvent, while not necessary, is preferred. Especially suitable inert organic solvents are alkanes such as hexane and cyclohexane and chlorinated hydrocarbons such as chloroform, ethylene dichloride and methylene chloride. Methylene chloride is especially preferred. Alkylation temperature is also not critical, but usually ranges from about 0° C. to about 50° C. and, preferably from about 18° C. to about 20° C.

Preferably, and especially when sulfuric acid is the Friedel-Crafts catalyst, the reaction product is extracted in the salt form with an inert organic solvent such as methylene chloride. The free amine can be obtained, if desired, by treatment with a suitable base such as sodium hydroxide, potassium hydroxide, sodium carbonate, potassium carbonate or calcium hydroxide.

The following Examples illustrate the invention.

EXAMPLE 1

800 g of 1-(2-methyl-3-phenyl-propyl)-piperidine are added to 3000 ml of methylene chloride. 2040 g of 95–96% sulfuric acid are then added dropwise over a 1.5 hour period with rapid stirring while cooling with brine to an internal temperature of 5°–10° C. The mixture is then warmed to 15°–20° C. internal temperature and 266 g of isobutylene are added over a 2 hour period. 1620 ml of water are then added dropwise while cooling with ice.

The red colored sulfuric acid solution is decolorized and the product dissolves as the hydrosulfate in the methylene chloride phase. The colorless sulfuric acid solution (the lower phase) is separated and then extracted with methylene chloride.

The combined methylene chloride extracts are washed with water. The product is separated from the methylene chloride phase by the portionwise addition, with stirring, of 1060 g of crystalline sodium carbonate. The methylene chloride phase is separated from the resulting aqueous phase and washed with water. The methylene chloride is then evaporated.

Distillation on a 30 cm Goodloe silver column yields pure 1-[3-(p-tert.-butyl-phenyl)-2-methyl-propyl]-piperidine, b.p. 118° C./0.07 Torr.

In an analogous manner:
1-[3-(p-tert.butyl-phenyl)-2-methyl-propyl]-3-methyl-piperidine, b.p. 116° C./0.02 Torr., is prepared from 1-(2-methyl-3-phenyl-propyl)-3-methyl-piperidine and isobutylene;

1-[3-(p-tert.butyl-phenyl)-2-methyl-propyl]-3,5-dimethyl-piperidine, b.p. 128°–130° C./0.001 Torr., is prepared from 1-(2-methyl-3-phenyl-propyl)-3,5-dimethyl-piperidine and isobutylene;

4-[3-(p-tert.butyl-phenyl)-2-methyl-propyl]-2,6-dimethyl-morpholine, b.p. 134°–136° C./0.03 Torr, is prepared from 4-(2-methyl-3-phenyl-propyl)-2,6-dimethyl-morpholine and isobutylene;

1-[3-[p-(2-chloro-1,1-dimethyl-ethyl)-phenyl]-2-methyl-propyl]-piperidine, b.p. 139°–140° C./0.04 Torr, is prepared from 1-(2-methyl-3-phenyl-propyl)-piperidine and 3-chloro-2-methyl-1-propene;

1-[3-[p-(2-chloro-1,1-dimethyl-ethyl)-phenyl]-2-methyl-propyl]-3,5-dimethyl-piperidine, b.p. 155°–156° C./0.04 Torr, is prepared from 1-(2-methyl-3-phenyl-propyl)-3,5-dimethyl-piperidine and 3-chloro-2-methyl-1-propene and 4-[3-[p-(2-chloro-1,1-dimethyl-ethyl)-phenyl]-2-methyl-propyl]-2,6-dimethyl-morpholine b.p. 155° C./0.04 Torr, is prepared from 4-(2-methyl-3-phenyl-propyl)-2,6-dimethyl-morpholine and 3-chloro-2-methyl-1-propene.

EXAMPLE 2

100 g of 1-(2-methyl-3-phenyl-propyl)-piperidine are added to 375 ml of methylene chloride. 255 g of 95–96% sulfuric acid are then added dropwise over a 1.5 hour period with rapid stirring while cooling with brine to an internal temperature of 10° C. The mixture is warmed to 20° C. and 42.5 g of tert.-butanol are added dropwise. The mixture is reacted at room temperature for 2 hours. The work-up is analogous to that described in Example 1. The crude product is purified by fractional distillation on a Goodloe silver column to yield pure 1-[3-(p-tert.butyl-phenyl)-2-methyl-propyl]-piperidine, b.p. 118° C./0.07 Torr.

In an analogous manner:

1-[3-(p-tert.butyl-phenyl)-2-methyl-propyl]-3-methyl-piperidine, b.p. 116° C./0.02 Torr is prepared from 1-(2-methyl-3-phenyl-propyl)-3-methyl-piperidine and tert.butanol;

1-[3-(p-tert.butyl-phenyl)-2-methyl-propyl]-3,5-dimethyl-piperidine b.p. 128°–130° C./0.001 Torr, is prepared from 1-(2-methyl-3-phenyl-propyl)-3,5-dimethyl-piperidine and tert.butanol;

4-[3-(p-tert.butyl-phenyl)-2-methyl-propyl]-2,6-dimethyl-morpholine, b.p. 134°–138° C./0.03 Torr, is prepared from 4-(2-methyl-3-phenyl-propyl)-2,6-dimethyl-morpholine and tert.butanol;

1-[3-(p-tert.amyl-phenyl)-2-methyl-propyl]-piperidine, b.p. 160° C./0.15 Torr, is prepared from 1-(2-methyl-3-phenyl-propyl)-piperidine and 2-methyl-2-butanol;

1-[3-(p-tert.amyl-phenyl)-2-methyl-propyl]-3-methyl-piperidine, b.p. 164° C./0.15 Torr, is prepared from 1-(2-methyl-3-phenyl-propyl)-3-methyl-piperidine and 2-methyl-2-butanol;

1-[3-(p-tert.amyl-phenyl)-2-methyl-propyl]-3,5-dimethyl-piperidine, b.p. 135° C./0.05 Torr, is prepared from 1-(2-methyl-3-phenyl-propyl)-3,5-dimethyl-piperidine and 2-methyl-2-butanol;

4-[3-(p-tert.amyl-phenyl)-2-methyl-propyl]-2,6-dimethyl-morpholine, b.p. 136°–138° C./0.04 Torr is prepared from 4-(2-methyl-3-phenyl-propyl)-2,6-dimethyl-morpholine and 2-methyl-2-butanol.

1-[3-[p-(1cyclohexyl-1-methyl)-phenyl]-2-methyl-propyl]-piperidine, b.p. 140° C./0.04 Torr, is prepared from 1-(2-methyl-3-phenyl-propyl)-piperidine and 2-methylcyclohexanol;

1-[3-p-(1-cyclohexyl-1-methyl)-phenyl]-2-methyl-propyl]-3,5-dimethyl-piperidine, b.p. 130°–132° C./0.04 Torr, is prepared from 1-(2-methyl-3-phenyl-propyl)-3,5-dimethyl-piperidine and 2-methyl-cyclohexanol and 4-[3-[p-(1-cyclohexyl-1-methyl)-phenyl]-2-methyl-propyl]-2,6-dimethyl-morpholine, b.p. 160°–162° C./0.07 Torr, is prepared from 4-(2-methyl-3-phenyl-propyl)-2,6-dimethyl-morpholine and 2-methyl-cyclohexanol.

EXAMPLE 3

A mixture of 1000 g of α-methyl-cinnamaldehyde, 10 liters of methanol and 640 g of piperidine are placed under a nitrogen atmosphere and 50 g of palladium/carbon are added thereto. The mixture is then hydrogenated while cooling with water to 30° C. internal temperature. Hydrogenation continued until the hydrogen uptake has been completed. The catalyst was filtered off and the methanol was distilled under vacuum. Distillation of the crude produce yielded pure 1-(2-methyl-3-phenyl-propyl)-piperidine, b.p. 92° C./0.04 Torr.

In an analogous manner:

1-(2-methyl-3-phenyl-propyl)-3-methyl-piperidine, b.p. 103° C./0.04 Torr, is prepared from α-methyl-cinnamaldehyde and 3-methyl-piperidine;

1-(2-methyl-3-phenyl-propyl)-3,5-dimethyl-piperidine, b.p. 94° C./0.03 Torr, is prepared from α-methyl-cinnamaldehyde and 3,5-dimethyl-piperidine and 4-(2-methyl-3-phenyl-propyl)-2,6-dimethyl-morpholine, b.p. 92° C./0.03 Torr, is prepared from α-methyl-cinnamaldehyde and 2,6-dimethyl-morpholine.

I claim:

1. A process for the preparation of a compound of the formula,

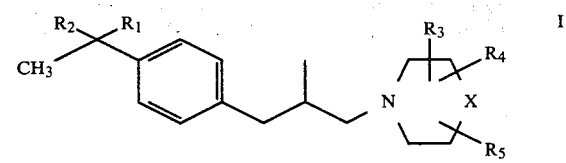

wherein $R_1$ and $R_2$ individually are lower alkyl of from 1 to 4 carbons or halo-(lower alkyl) of from 1 to 4 carbons or $R_1$ and $R_2$ together with the carbon to which they are attached form a 3- to 7-membered cycloalkyl ring or lower alkyl substituted cycloalkyl of from 4 to 9 carbons, $R_3$, $R_4$ and $R_5$ individually are hydrogen or lower alkyl of from 1 to 4 carbons and X is methylene or oxygen, and salts of those compounds which are basic, which comprises reacting, in the presence of a Friedel-Crafts catalyst, a compound of the formula,

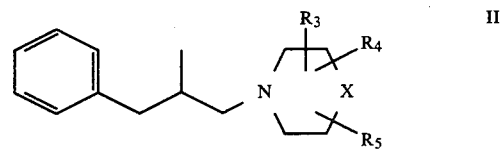

wherein $R_3$, $R_4$, $R_5$ and X have the significance given above, with a compound selected from the group consisting of a secondary alcohol and a tertiary alcohol which forms a carbonium ion of the formula,

wherein $R_1$ and $R_2$ have the significance given above, in a chlorinated hydrocarbon solvent at a temperature of from about 0° C. to about 50° C. to form, as a reaction product, a morpholine or piperidine derivative of the formula I.

2. The process of claim 1 wherein the catalyst is sulfuric acid.

3. The process of claim 1 wherein the reaction product is extracted in its salt form using an inert organic solvent.

4. The process of claim 1 wherein the compound which form the carbonium ion of formula III is an alcohol selected from the group consisting of tert.-butanol, 2-methyl-2-butanol, 2-methylcyclohexanol and 4-methylcyclohexanol.

5. The process of claim 1 wherein the compound of formula II is selected from the group consisting of 1-(2-methyl-3-phenyl-propyl)-piperidine; 1-(2-methyl-3-phenyl-propyl)-3-methyl-piperidine, 1-(2-methyl-3-phenyl-propyl)-3,5-dimethyl-piperidine and 4-(2-methyl-3-phenyl-propyl)-2,6-dimethyl-morpholine.

6. A process for the preparation of a compound of the formula,

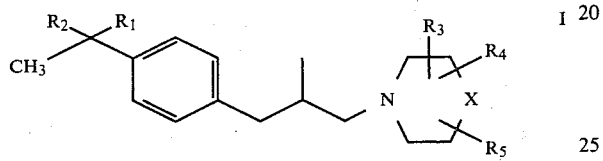
I wherein $R_1$ and $R_2$ individually are lower alkyl of from 1 to 4 carbons, $R_3$, $R_4$ and $R_5$ individually are hydrogen or lower alkyl of from 1 to 4 carbons and X is methylene or oxygen, and salts of those compounds which are basic, which comprises reacting, in the presence of a Friedel-Crafts catalyst, a compound of the formula,

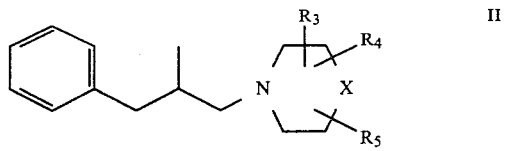
II wherein $R_3$, $R_4$, $R_5$ and X are as defined above, with tertiary alcohol which forms a carbonium of the formula,

III wherein $R_1$ and $R_2$ are as defined above, in a chlorinated hydrocarbon solvent at a temperature of from about 0° C. to about 50° C., to form, as a reaction product, a morpholine or piperidine derivative of the formula I.

* * * * *